United States Patent
Kim

(10) Patent No.: US 8,187,167 B2
(45) Date of Patent: May 29, 2012

(54) MONITORING APPARATUS FOR LAPAROSCOPIC SURGERY AND DISPLAY METHOD THEREOF

(76) Inventor: Jae-Hwang Kim, Daegu (KR)

( * ) Notice: Subject to any disclaimer, the term of this patent is extended or adjusted under 35 U.S.C. 154(b) by 1431 days.

(21) Appl. No.: 11/660,934

(22) PCT Filed: Oct. 18, 2005

(86) PCT No.: PCT/KR2005/003464
§ 371 (c)(1),
(2), (4) Date: Apr. 9, 2007

(87) PCT Pub. No.: WO2006/046809
PCT Pub. Date: May 4, 2006

(65) Prior Publication Data
US 2008/0103354 A1 May 1, 2008

(30) Foreign Application Priority Data
Oct. 28, 2004 (KR) ........................ 10-2004-0086697

(51) Int. Cl.
*A61B 1/00* (2006.01)
*A61B 1/04* (2006.01)

(52) U.S. Cl. ........................................ 600/103; 600/117
(58) Field of Classification Search .................... 348/61, 348/794, 841, 831, 836; 600/101, 102, 118
See application file for complete search history.

(56) References Cited

U.S. PATENT DOCUMENTS

| 5,351,676 | A | 10/1994 | Putman |
| 2001/0030683 | A1* | 10/2001 | Howell et al. ................... 348/61 |
| 2002/0032365 | A1 | 3/2002 | Hasegawa et al. |
| 2004/0070822 | A1* | 4/2004 | Shioda et al. ................ 359/372 |
| 2005/0110911 | A1* | 5/2005 | Childrey et al. .............. 348/794 |
| 2006/0071135 | A1* | 4/2006 | Trovato .................... 248/289.11 |

* cited by examiner

*Primary Examiner* — Philip R Smith
(74) *Attorney, Agent, or Firm* — Birch, Stewart, Kolasch & Birch, LLP

(57) ABSTRACT

A monitor apparatus for a laparoscopic surgery rotates images captured by a laparoscope as an endoscope and displayed on monitors for the laparoscopic surgery clockwise or counter-clockwise according to commands for rotating the images by surgeons who use image rotation manipulation parts such that the images of surgical devices displayed on the monitors are arranged in the direction where the surgeons can actually manipulate the laparoscopic surgical devices most conveniently.

3 Claims, 6 Drawing Sheets

[Fig. 1]
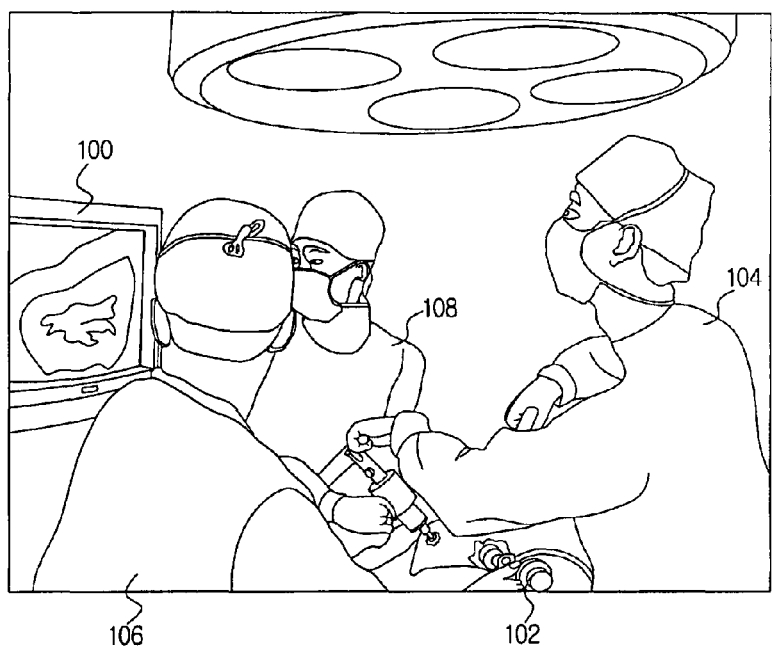
[Fig. 2]
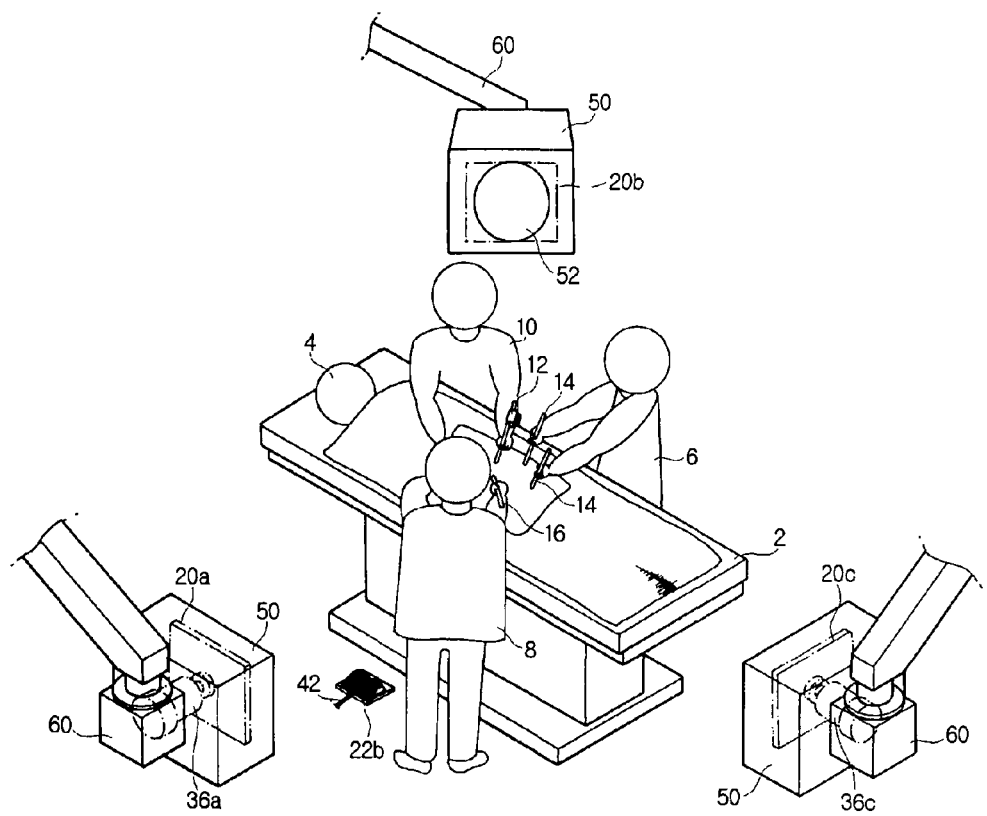

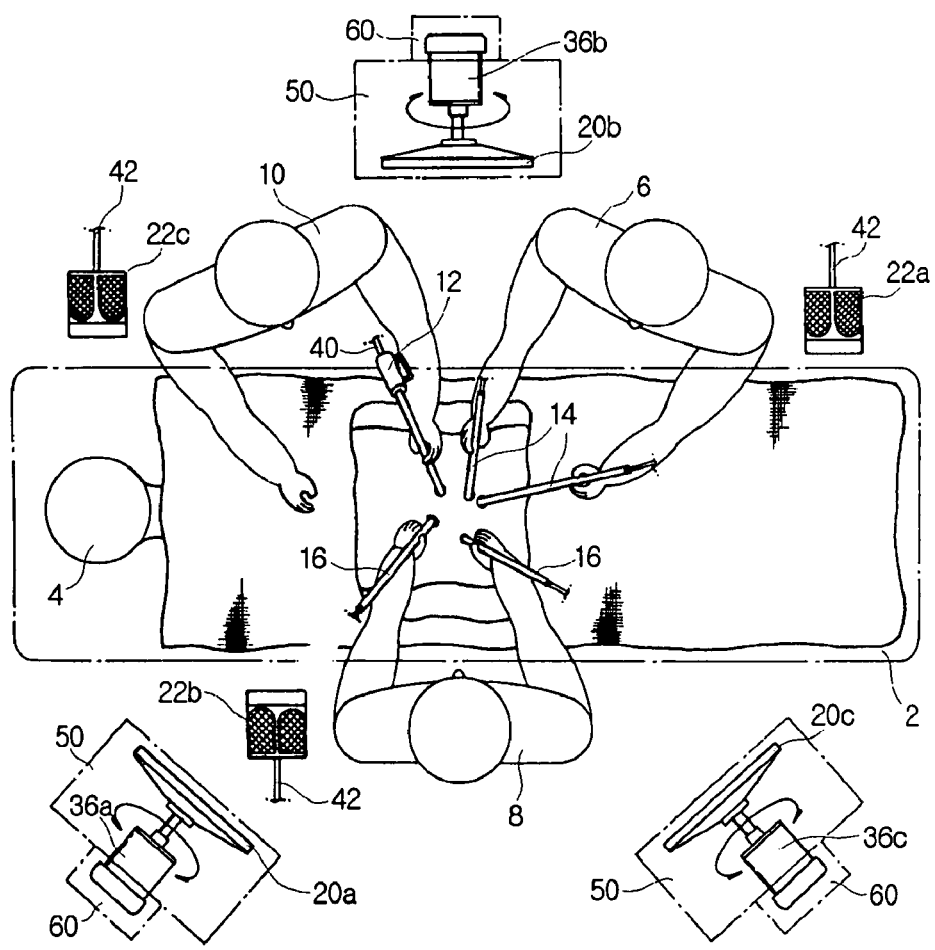
[Fig. 3]

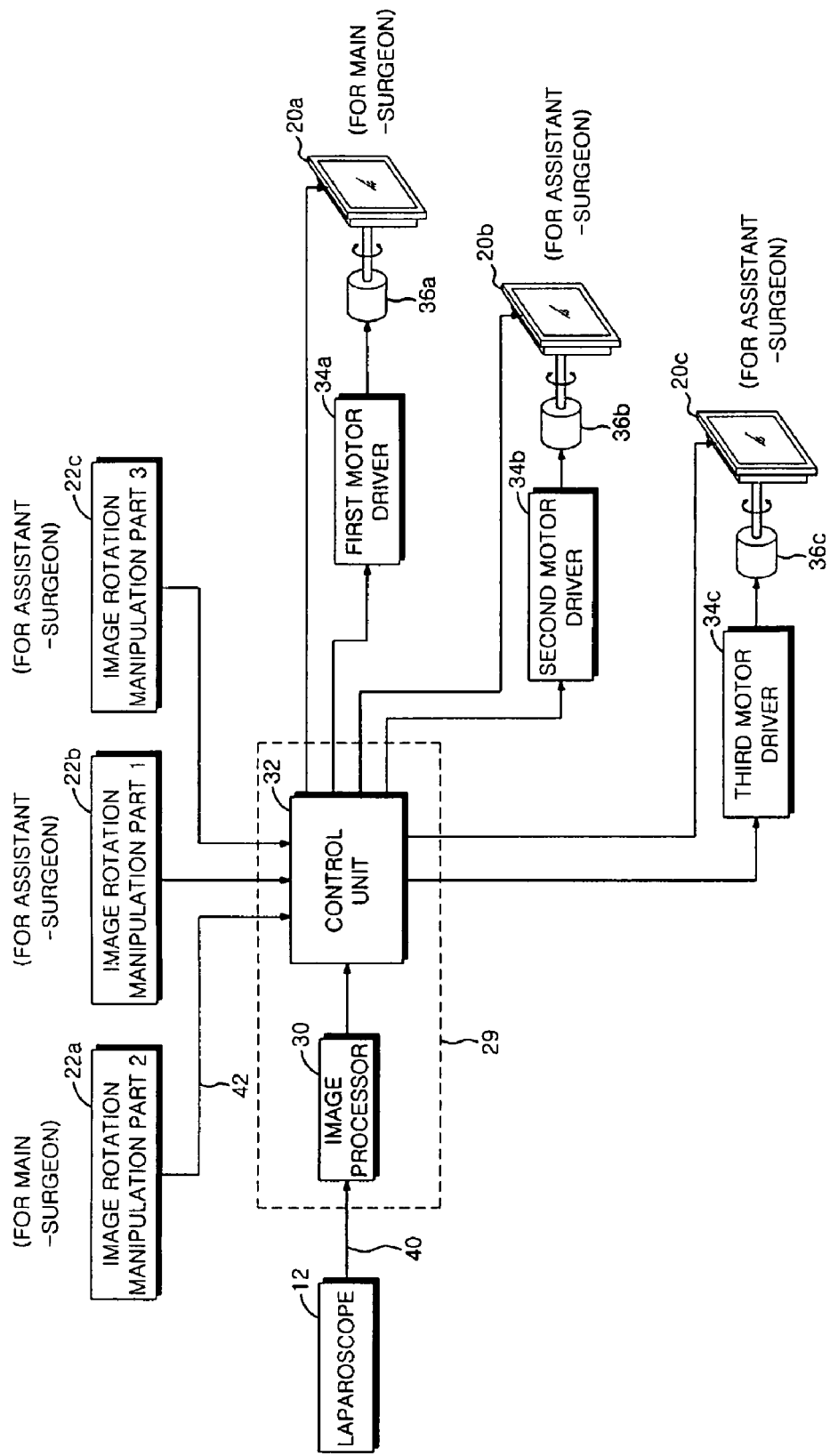
[Fig. 4]

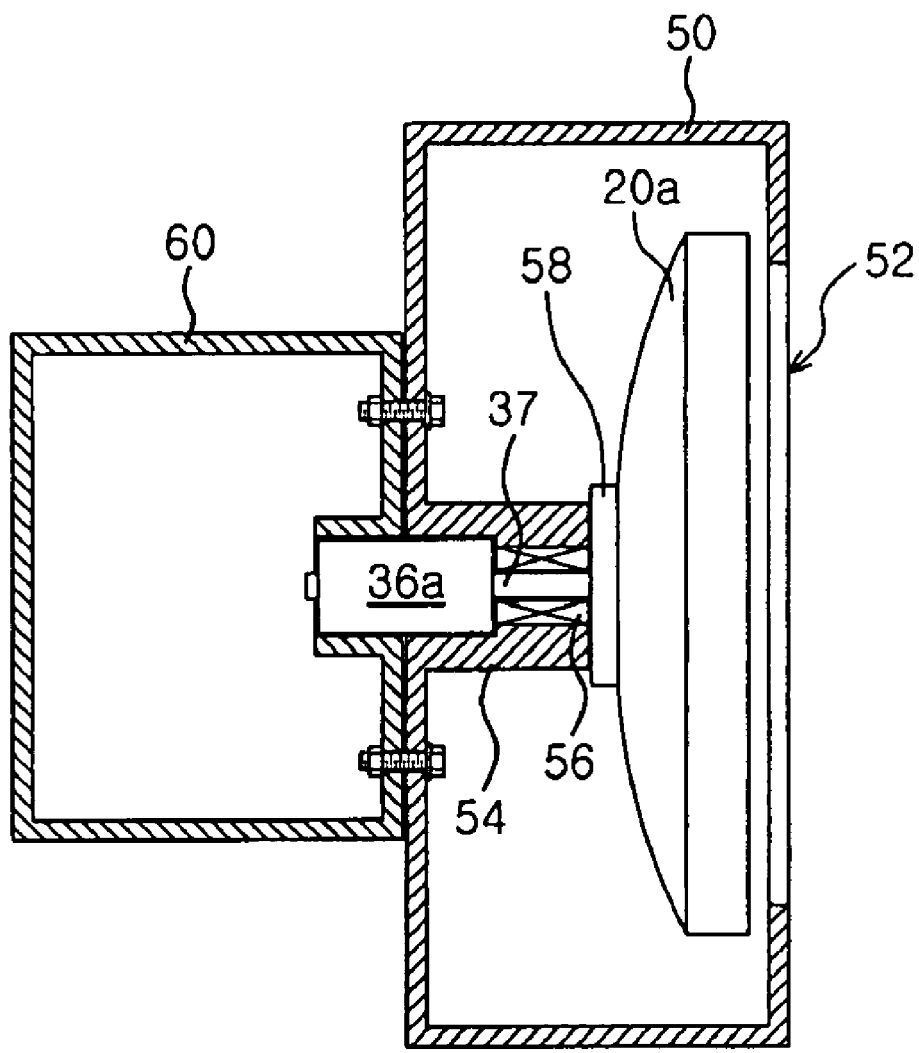
[Fig. 5]

[Fig. 6]
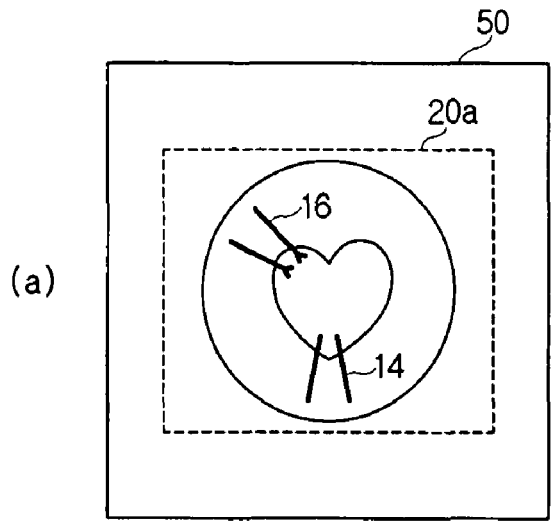
(a)
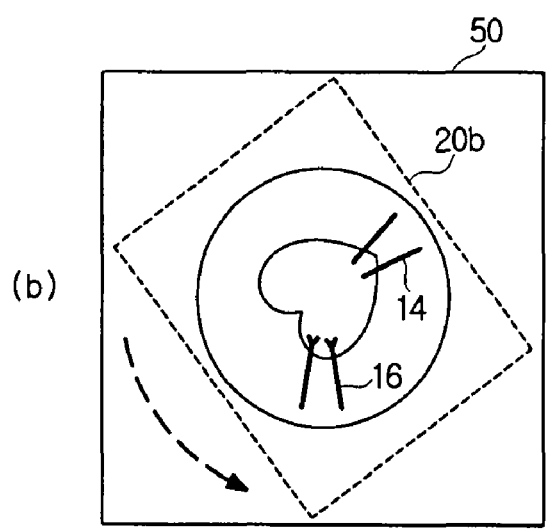
(b)
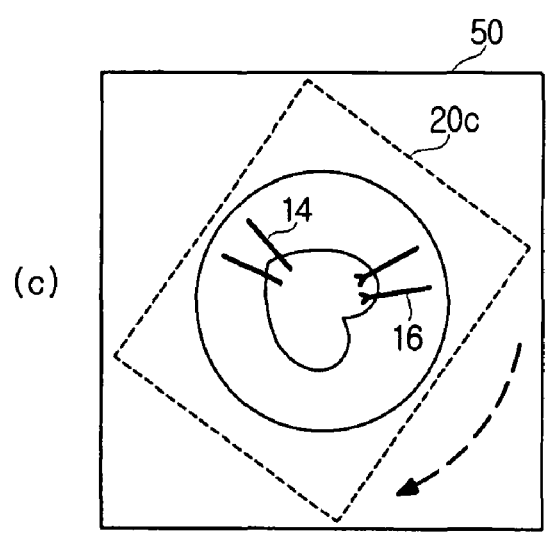
(c)

[Fig. 7]
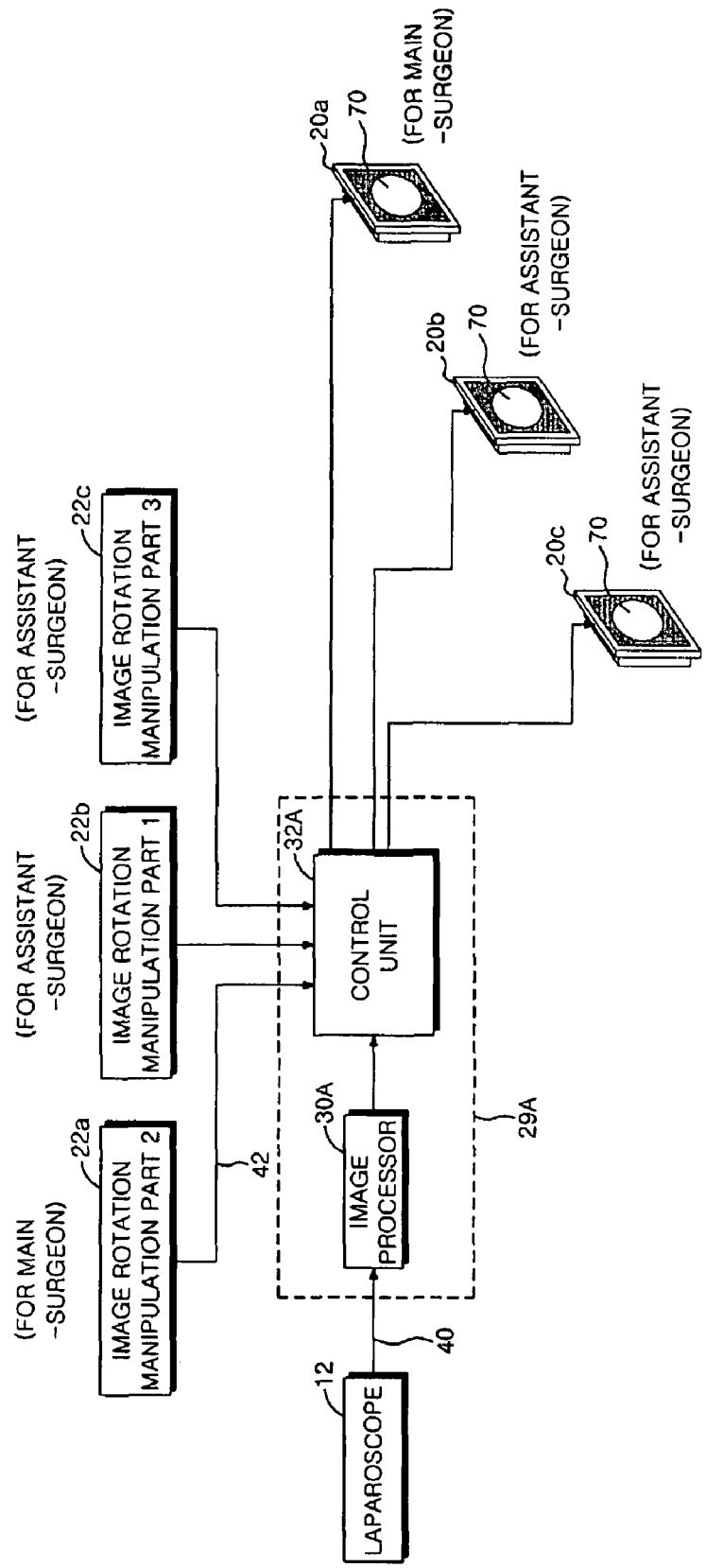

MONITORING APPARATUS FOR LAPAROSCOPIC SURGERY AND DISPLAY METHOD THEREOF

TECHNICAL FIELD

The present invention relates to a medical apparatus, and more particularly, to an improvement of a medical apparatus for laparoscopic surgery.

BACKGROUND ART

Laparoscopic surgery is a high technological surgery whereby a hole about 1 cm in size is made in the vicinity of the navel and an operation is performed by inserting a laparoscope through the hole for seeing inside the patient's belly. This medical field is currently experiencing many developments.

The recently developed laparoscopes can provide more clear and enlarged images than those seen by a naked eye and have been developed to allow any surgery using surgical apparatuses specifically invented for the laparoscopes while watching monitors.

Moreover, since the laparoscopic surgery has an operation extent similar to that of an abdominal operation, involves less complications than the abdominal operation, can start to treat the operated region after the surgery in a shorter time than the abdominal operation, and has a capability of maintaining stamina and/or immune function of the patient superior than the abdominal surgery, the laparoscopic surgery can reduce recurrence of cancer in the future. Due to these reasons, the laparoscopic surgery is being gradually authorized as a standard surgical procedure for treatment of colon cancer in U.S.A. and Europe.

However, the laparoscopic surgery is more difficult than the conventional abdominal surgery. The reasons are that apparatuses for the laparoscopic surgery are unfamiliar, the laparoscopic surgery provides only two-dimensional images and mirror images, and a surgeon cannot directly touch the part of the patient that is being operated on.

DISCLOSURE OF INVENTION

Technical Problem

Therefore, the present invention has been made in view of the above and/or other problems, and it is an object of the present invention to provide a monitor apparatus for laparoscopic surgery capable of solving difficulties when the laparoscopic surgery is performed while watching a monitor and a method of displaying the region being operated on.

Technical Solution

In accordance with the present invention, the above and other objects can be accomplished by the provision of a monitor apparatus for a laparoscopic surgery in which a controller controls images, captured by a laparoscope as an endoscope and displayed on monitors, to rotate clockwise or counterclockwise according to surgeons' command using image manipulation parts such that the images are arranged in the directions where the surgeons can actually manipulate the laparoscopic surgical devices most conveniently while watching the images displayed on the monitors.

ADVANTAGEOUS EFFECTS

According to the present invention, the difficulty of the laparoscopic surgery watching a monitor by multiple surgeons is solved by rotating the monitor.

BRIEF DESCRIPTION OF THE DRAWINGS

These and/or other objects and advantages of the present invention will become apparent and more readily appreciated from the following description of the embodiments, taken in conjunction with the accompanying drawings, in which:

FIG. 1 is a view illustrating a conventional laparoscopic surgery;

FIGS. 2 and 3 are views illustrating a monitor apparatus for laparoscopic surgery according to a preferred embodiment of the present invention;

FIG. 4 is a block diagram illustrating the monitor apparatus for laparoscopic surgery according to the preferred embodiment of the present invention;

FIG. 5 is a side sectional view illustrating an assembly of a driving motor 36a and a monitor 20a for laparoscopic surgery;

FIG. 6 is a view illustrating monitors for the laparoscopic surgery rotated such that the monitor screens are aligned with the surgeons themselves; and FIG. 7 is a block diagram illustrating the rotation of images to be displayed on the monitors using an image processing according to another preferred embodiment of the present invention.

BEST MODE FOR CARRYING OUT THE INVENTION

Hereinafter, a monitor apparatus for laparoscopic surgery and displaying method thereof according to the preferred embodiment of the present invention will be described with reference to the accompanying drawings. It is noticed that the same numerals in the drawings are assigned to the same components. Moreover, the description for the conventional function and structure that may confuse spirit of the present invention will be omitted.

One of the difficulties of the laparoscopic surgery is that a surgeon must perform the laparoscopic surgery using surgical devices for the laparoscopic surgery while watching a monitor.

As shown in FIG. 1, when a single monitor 100 for the laparoscopic surgery is provided, an image displayed on the monitor 100 is different according to the position into which the laparoscope as an endoscope is inserted. Generally, the surgeon inserts the laparoscope. At that time, the surgeon can normally perform the laparoscopic surgery with watching the image displayed on the monitor 100 chiefly disposed at the opposite side. However, different from the main surgeon 104, assistant surgeons 106 and 108 at other sides must twist their body to watch the images displayed on the monitors, as well as since surgical devices of the assistant surgeons 106 and 108 are displayed at the upper sides or the left or right sides on the monitors, the assistant surgeons have difficulty to perform the laparoscopic surgery due to watching the monitors.

When instead of a single monitor as shown in FIG. 1, two or three monitors are arranged to form a triangle, it is much more convenient for the main surgeon and the assistant surgeons to perform the laparoscopic surgery by watching the respective monitors without twisting their bodies. However, the surgical devices and hands of the assistant surgeons are often displayed on the monitors different from the actual positions. In other words, since the upper and lower sides or the right and left sides of the images are reversed on the monitors, it is difficult for the assistant surgeons to perform the laparoscopic surgery while watching the monitors. Thus, in order to skillfully perform the laparoscopic surgery, a great deal of laparoscopic surgical experience is required, and it is difficult for novices and moderately skilled surgeons of laparoscopic surgery to perform the laparoscopic surgery. Therefore, for the successful laparoscopic surgery, gathering a laparoscopic surgical team including skilled assistants (assistant surgeons) is important preparation for the laparoscopic surgery.

Since the surgical devices and hands are displayed at the upper sides or the right and left sides in the monitors, it is difficult for the assistant surgeons to perform the laparoscopic surgery while watching the images displayed on the monitors.

In the preferred embodiment of the present invention, visual images displayed on the monitors are provided such that the main surgeon and the assistant surgeons can conveniently perform the laparoscopic surgery.

To this end, in the present invention, images captured by a laparoscope as an endoscope and displayed on a monitor are rotated clockwise or counterclockwise by a controller according to a user's command using an image manipulation part such that the images are arranged in the direction where the surgeon can actually manipulate the laparoscopic surgical devices most conveniently while watching the images displayed on the monitor.

A method of rotating images for the laparoscopic surgery performed by the controller includes the steps of 1) checking whether there is a command for rotation of the images for the laparoscopic surgery displayed on respective monitors from at least one of image rotation manipulation parts by a surgeon, and 2) when there is a surgeon's command for the rotation of the image, rotating an image displayed on one of the monitors corresponding to the image rotation manipulation part commanding the rotation of the corresponding image clockwise or counterclockwise based on rotation angle information such that the displayed image watched by the surgeon is similarly arranged in the direction where laparoscopic surgical devices which are used by the surgeon are actually arranged.

The method of rotating the image displayed on the monitor clockwise or counter-clockwise is roughly divided into a method of directly rotating the monitor (See FIGS. 2 to 6) and a method of rotating the image displayed on the monitor using image processing (See FIG. 7).

Firstly, the method of directly rotating the monitor will be described in detail with reference to FIGS. 2 to 6, as follows.

FIGS. 2 and 3 are views illustrating a monitor apparatus for laparoscopic surgery according to a preferred embodiment of the present invention, and FIG. 5 is a block diagram illustrating the monitor apparatus for laparoscopic surgery according to the preferred embodiment of the present invention.

As shown in FIGS. 2 to 4, a total number of surgeons performing the laparoscopic surgery is three, including a main surgeon and assistant surgeons, and three monitors for the laparoscopic surgery are installed corresponding to the number of the surgeons. However, those skilled in the art could understand that the drawings do not limit the scope of the present invention and are provided only for the illustrative purpose. Those skilled in the art could understand that the number of the main and assistant surgeons may be two or more as could be the number of the monitors.

Firstly, referring to FIGS. 2 and 3, a singe main surgeon 6 and two assistant surgeons 8 and 10 stand about a patient 4 lying on an operating table 2 to form a triangle and perform the laparoscopic surgery using a laparoscope 12 and surgical devices 14 and 16 for the laparoscopic surgery.

In this preferred embodiment of the present invention, monitors 20a, 20b, and 20c are installed on the opposite sides of the respective surgeons 6, 8, and 10 so that the main surgeon 6 and the assistant surgeons 8 and 10 can perform the laparoscopic surgery while watching the respective monitors 20a, 20b, and 20c, wherein driving motors 36a, 36b, and 36c respectively installed at the rear sides of the monitors 20a, 20b, and 20c to rotate the respective monitors 20a, 20b, and 20c clockwise or counter-clockwise so that the surgeons can conveniently perform the laparoscopic surgery while watching the images displayed on the respective monitors 20a, 20b, and 20c.

In order to rotate the respective monitors 20a, 20b, and 20c for the laparoscopic surgery clockwise or counterclockwise, on the ground where the respective surgeons 6, 8, and 10 stand, image rotation manipulation parts 22a, 22b, and 22c corresponding to the respective monitors 20a, 20b, and 20c are installed. The image rotation manipulation parts 22a, 22b, and 22c can be implemented by foot switches respectively including a right button and a left button. When the main surgeon or the assistant surgeon presses the right button of one of the foot switch, the monitor installed in the opposite side of the corresponding surgeon is rotated clockwise slowly, and when pressing the left button of one of the foot switches, the monitor installed in the opposite side of the corresponding surgeon is rotated counter clockwise slowly to maximum 180 degrees.

In this preferred embodiment of the present invention, although the monitors are rotated using the foot switches, the monitors can be rotated by the user's foot, hands, or voice.

As shown in FIGS. 2 and 3, wires 40 and 42 are connected to the laparoscope 12 and the image rotation manipulation parts 22a, 22b, and 22c. The wires 40 and 42 are partially depicted in FIGS. 2 and 3, but are connected also to a controller 29 (See FIG. 4). Although the connection between the laparoscope 12 and the controller 29 and between the image rotation manipulation parts 22a, 22b, and 22c and the controller 29 can be implemented by wires or short-range wireless communications, since signals could interfere with each other, preferably the connections are implemented by wires.

Referring to FIG. 4, the controller 29 includes an image processor 30 and a control unit 32. An image captured by the laparoscope 12 is transmitted to the controller 29 and is processed by the image processor 30 of the controller 29, and after this, the processed image is transmitted to the control unit 32. The control unit 32 controls the image processed by the image processor 30 to be displayed on the respective monitors 20a, 20b, and 20c for the laparoscopic surgery.

Moreover, the control unit 32 drives motor drivers 34a, 34b, and 34c in response to the operation signals for rotating the respective monitors from the image rotation manipulation parts 22a, 22b, and 22c. The motor drivers 34a, 34b, and 34c rotate respective driving motors 36a, 36b, and 36c clockwise or counterclockwise according to the control signals from the control unit 32.

Each of the driving motors 36a, 36b, and 36c includes a direct current motor and a reducer, and slowly rotates the corresponding one of the monitors 20a, 20b, and 20c clockwise or counterclockwise when a corresponding surgeon generates a command to rotate using the corresponding one of the image rotation manipulation parts 22a, 22b, and 22c by foot.

Preferably, the monitors 20a, 20b, and 20c installed to the driving motors 36a, 36b, and 36c are one of light and thin flat type displays such as plasma display panels (PDP), flat panel displays (FPD), thin film transistor liquid crystal displays (TFT LCD), or the like.

The assembly of the driving motors 36a, 36b, and 36c and the monitors 20a, 20b, and 20c for the laparoscopic surgery will be described in detail with reference to FIG. 5 as follows.

As shown in FIGS. 2 and 3, the monitor 20a is disposed in a protective box 50 having a circular opening 52 formed in the front side thereof, and the driving motor 36a is accommodated in a support 54 integrally formed with the rear side of the protective box 50 and a driving shaft 37 of the driving motor 36a is inserted into an insert hole of the support 54 such that the leading end of the driving shaft 37 is coupled with a fixing plate 58 attached to the monitor 20a. In the insert hole of the support 54, bearings 56 are installed so that the monitor 20a can be smoothly rotated.

The rear side of the protective box 50 is coupled with an arm 60 for adjusting the positions, the heights, and the right and left inclined angles of the monitors 20a, 20b, and 20c for the laparoscopic surgery. Thus, the protective boxes 50 maintain a fixed state and only the monitors 20a, 20b, and 20c are rotated clockwise or counter-clockwise in the protective boxes 50. The arm 60 may be suspended to the roof or on the ground.

For example, the monitors 20a, 20b, and 20c for the laparoscopic surgery may be desktop type monitors that stand on the ground or hanger type monitors that are hung on the arm 60 suspended to the roof.

The opening 54 formed in the front side of the protective box 50 has a circular shape so that the surgeons cannot feel apprehensive when the monitors 20a, 20b, and 20c are being or have been rotated clockwise or counterclockwise and can concentrate on the images displayed on the monitors 20a, 20b, and 20c.

As described above, according to the monitor apparatus for the laparoscopic surgery, the main surgeon 6 and the assistant surgeons 8 and 10 can rotate the monitors 20a, 20b, and 20c for the laparoscopic surgery in the protective boxes 50 clockwise or counterclockwise to be aligned with themselves using the foot switches as the manipulation parts for rotating the monitors.

FIG. 6 is a view illustrating monitors for the laparoscopic surgery rotated such that the monitor screens are aligned with the surgeons themselves.

Referring to FIG. 6, (a) of FIG. 6 is a view illustrating an original displayed image aligned with the main surgeon 6 of FIG. 2.

(b) of FIG. 6 is a view illustrating that a monitor 20b for the laparoscopic surgery is rotated counterclockwise such that the monitor 20b is aligned with an assistant surgeon 8 in a ten o'clock direction of FIG. 2. As a result, the laparoscopic surgical devices 16 of the assistant surgeon 8 displayed on the monitor 20b are located in a six o'clock direction.

(c) of FIG. 6 is a view illustrating that a monitor 20c for the laparoscopic surgery is rotated counterclockwise such that the monitor 20c is aligned with an assistant surgeon 10 in a two o'clock direction of FIG. 2. As a result, the laparoscopic surgical devices 18 of the assistant surgeon 10 displayed on the monitor 20c are located in a six o'clock direction.

Next, the method of rotating the image displayed on the monitors for the laparoscopic surgery using image processing and displaying the processed images according to another preferred embodiment of the present invention will be described in detail with reference to FIG. 7 as follows.

FIG. 7 is a block diagram illustrating the rotation of images to be displayed on the monitors using image processing according to another preferred embodiment of the present invention.

Although the structure shown in FIG. 7 is similar to that shown in FIGS. 2 to 4, the difference therebetween is that the driving motors 36a, 36b, and 36c for rotating the monitors 20a, 20b, and 20c for the laparoscopic surgery, the first, second, and third motor drivers 34a, 34b, and 34c, and the protective box 60 having the opening as shown in FIGS. 2 to 4 are omitted in FIG. 7.

Moreover, the functions of an image processor 30A and a control unit 32A of a controller 29A are slightly different from those of the image processor 30 and the control unit 32 of the controller 29 as shown in FIGS. 2 to 4.

As shown in FIG. 7, the controller 29A includes the image processor 30A and the control unit 32A and may be implemented by a console box.

The image processor 30A processes images captured by the laparoscope 12 such that the captured images are rotated according to the image rotation angle control from the control unit 32A and are transmitted to the control unit 32A. The control unit 32A transmits the control information about the image rotation angle corresponding to the rotation command from the image rotation manipulation parts 22a, 22b, and 22c to the image processor 30A and controls the images rotated by the image processor 30A to be displayed on the monitors 20a, 20b, and 20c for the laparoscopic surgery. Since the images processed to be rotated are arranged such that the directions of the images of the laparoscopic surgical devices displayed on the monitors for the laparoscopic surgery are similar to or identical to the actual directions of the surgical devices, the surgeons can conveniently perform the laparoscopic surgery.

Moreover, the control unit 32A forms circular effective visual windows 70 in the screens of the monitors for the laparoscopic surgery such that the corresponding images are displayed through the effective visual windows 70. The areas outside the effective visual windows 70 of the screens of the monitors 20a, 20b, and 20c are displayed in black by the control unit 32A. Thus, since the surgeons watch images displayed within the effective visual windows 70, the surgeons can feel stability regardless of the rotation of the images.

Since, when the controller 29A is made in the form of a console box as described in another preferred embodiment of the present invention and is distributed to consumers, the console box type controller 29A can be combined to the laparoscopic surgery, the console box type controller can be immediately applied to the medical field.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Industrial Applicability

The present invention can be applied to the laparoscopic surgery.

The invention claimed is:

1. A monitor apparatus for laparoscopic surgery comprising:
    a laparoscope as an endoscope;
    at least one monitor for laparoscopic surgery, the at least one monitor having a display on a front side for displaying an image;
    an image rotation manipulation part; and a controller for controlling images captured by the laparoscope and displayed on the at least one monitor to rotate the images clockwise or counterclockwise about an axis perpendicular to the front side of the at least one monitor according to a user's command;
a protective box having a circular opening formed in the front sides and accommodating the at least one monitor,
wherein the controller comprises:
- at least one driving motor for rotating the at least one monitor for the laparoscopic surgery clockwise or counterclockwise;
- at least one motor driving part for rotating the at least one driving motor; and
- a controlling part for driving the at least one motor driving part according to commands from the image rotation manipulation part.

2. A monitor apparatus for laparoscopic surgery comprising:
- a laparoscope as an endoscope;
- at least one monitor for displaying images captured by the laparoscope and installed on an arm located around an operation table;
- a driving motor mounted between a rear side of the at least one monitor and the arm; and
- a controller for driving the driving motor according to monitor rotation commands by surgeons, using an image rotation manipulation part assigned to the surgeons, to rotate the at least one monitor clockwise or counterclockwise.

3. The monitor apparatus as set forth in claim 2, wherein the controller rotates the at least one monitor about an axis perpendicular to the front of the at least one monitor.

* * * * *